United States Patent [19]
Rheinberger et al.

[11] Patent Number: 5,936,006
[45] Date of Patent: Aug. 10, 1999

[54] FILLED AND POLYMERIZABLE DENTAL MATERIAL

[75] Inventors: Volker Rheinberger, Vaduz; Norbert Moszner, Eschen, both of Liechtenstein; Urs Karl Fischer, Arbon, Switzerland

[73] Assignee: Ivoclar AG, Liechtenstein

[21] Appl. No.: 08/837,677

[22] Filed: Apr. 22, 1997

[30] Foreign Application Priority Data

Apr. 26, 1996 [DE] Germany ............... 196 17 931

[51] Int. Cl.$^6$ ...................................................... A61K 6/08
[52] U.S. Cl. ................................................................ 523/116
[58] Field of Search ............................................... 523/116

[56] References Cited

U.S. PATENT DOCUMENTS

| | | | |
|---|---|---|---|
| 4,503,169 | 3/1985 | Randklev | 523/115 |
| 4,933,202 | 6/1990 | Rheinberger | 427/2 |
| 5,177,120 | 1/1993 | Hare | 523/109 |
| 5,318,999 | 6/1994 | Mitra | 523/116 |
| 5,332,779 | 7/1994 | Mohri | 524/790 |
| 5,502,087 | 3/1996 | Tateosian | 523/115 |

FOREIGN PATENT DOCUMENTS

| | | |
|---|---|---|
| 0 315 186 A2 | 10/1989 | European Pat. Off. . |
| 195 08 586 A1 | 9/1996 | Germany . |
| 6-191827 | 4/1982 | Japan . |
| 7-291817 | 7/1995 | Japan . |

*Primary Examiner*—Edward J. Cain
*Attorney, Agent, or Firm*—Nixon, Hargrave, Devans & Doyle LLP

[57] ABSTRACT

A filled and polymerizable dental material is described which contains a sol of $SiO_2$ particles in a liquid, organic dispersion agent, the $SiO_2$ particles being organically surface modified, having an average size of 10 to 100 nm and being non-agglomerated.

15 Claims, No Drawings

FILLED AND POLYMERIZABLE DENTAL MATERIAL

FIELD OF THE INVENTION

The invention relates to a filled and polymerizable dental material which can be used in particular in the form of filling composites, fixing cements or adhesives.

BACKGROUND OF THE INVENTION

The properties of dental filling composites depend on the structure of the organic matrix but also on the properties of the fillers used. Particle size, size distribution, particle shape, type of particle surface, chemical composition, the nature of any surface modification and optical properties of the fillers and also the total fillers content have a major influence on the overall properties of the composite (cf J. F. Roulet, Degradation of Dental Polymers, Karger, Basel 1987, page 10).

A high strength of the dental filling composites as well as a low polymerization shrinkage can be achieved above all by a high degree of filling. The optimum degree of filling is also determined by the necessary consistency of the composite pastes which are used in practice. These must be such that an optimum introduction of the materials into the tooth cavity as well as an optimum processing is possible. It is known that, as a result of the addition of fillers to the matrix monomer mixture, viscosity increases with the filler content, the thickening effect e.g. of the highly dispersed silicic acid, which according to DE-C-24 03 211 is used as filler in dental compositions, growing as the primary particle size decreases and the BET surface increases. Currently used microfiller composites are consequently characterized by a degree of filling with inorganic fillers of ca. 50 wt. % and hybrid composites by a degree of filling of ca. 80 wt. %.

By contrast, lower viscosities are necessary in the case of composite-based fixing cements compared with the corresponding permanent filling composites, so that only a lower degree of filling can be achieved. A highly fluid consistency is generally necessary for dental adhesives, for which reason the addition of fillers must be completely dispensed with as a rule in these.

The use of products of sol-gel processes as a constituent of dental materials is known. Thus, dental materials which contain heterosiloxanes as filler of small particle size are described in DE-C-39 13 252, EP-B-394 794 and EP-B-523 545. The heterosiloxanes used are prepared by cocondensation of suitable silanes with metal alkoxides as statistical copolycondensates, block copolycondensates or so-called mixed copolycondensates. It is necessary that, after carrying out the sol-gel process, the solids produced are separated, washed, dried, ground while being kept at a certain temperature and in some cases also functionalized by surface silanization. These process steps influence the properties of the finally obtained filler in such a way that the latter is present merely in agglomerated form.

Analogous sol-gel fillers based on heteropolysiloxanes can be used for dental filling materials according to EP-B-381 961.

Also known, from DE-A-41 33 494, are dental materials based on polymerizable polysiloxanes which are likewise obtained by the sol-gel process from hydrolytically condensable silanes. The resins obtained after condensation are highly viscous and can hardly be filled further.

Compositions based on organically modified silicic acid-poly-condensates, which can be used for coating teeth and denture parts, are known from WO 92/16183. It is necessary for the obtained inorganic/organic precondensates to be diluted with a solvent in order to control the viscosity of the compositions.

GB-A-2 257 438 discloses products of the sol-gel process for the glass-like coating of teeth.

Finally, it is also known that the preparation of $SiO_2$ sols by hydrolysis and condensation of suitable precursors, e.g. condensable silanes, is possible. The sol particle formation depends among other things on the nature of the precursors, the nature of the reaction medium, the pH value, the catalyst or the amount of water used (cf C. J. Brinker, G. W. Scherer, Sol-Gel-Science, Academic Press, Boston 1990, pages 99 et seq. and 617 et seq.).

Silica sols are aqueous solutions of colloidal, amorphous $SiO_2$ which as a rule contain 10 to 50 wt. % $SiO_2$ particles having a diameter of 5 to 150 nm (cf Ullmann's Encyklopädie der technischen Chemie, 4th edition, Volume 21, Verlag Chemie, Weinheim 1982, pages 456 et seq.). It is possible to silanize the particles of these aqueous silica sols e.g. with 3-(methacryloyloxy)-propyltrimethoxysilane and carry out a solvent replacement, e.g. with isopropanol or monomer (cf L. N. Lewis et al., Polym. Mat. Sci. Techn., Proceed. Amer. Chem. Soc., 72 (1995), page 583).

SUMMARY OF THE INVENTION

The object of the invention now is to make available a filled and polymerizable dental material which, compared with materials having conventional fillers, shows a lower viscosity, improved mechanical properties and a reduced polymerization shrinkage.

This object is achieved by the filled and polymerizable dental material of the invention according to Claims 1 to 12.

Furthermore, the invention also relates to the use of a filled and polymerizable material as dental material according to Claim 13.

DETAILED DESCRIPTION OF THE INVENTION

The filled and polymerizable dental material according to the invention is characterized in that it (a) contains a sol of amorphous $SiO_2$ particles in a liquid, organic dispersion agent, the $SiO_2$ particles being organically surface modified, having an average size of 10 to 100 nm and being non-agglomerated.

The fact that the $SiO_2$ particles are present in non-agglomerated form can be demonstrated e.g. by means of transmission electron microscopy (TEM). The average size of the particles is also measured by means of TEM.

In the following, the sol (a) is also referred to as silica organosol.

The dental material according to the invention usually contains 1 to 50 wt. % of the sol (a). The $SiO_2$ particles content of the sol (a) is usually 10 to 70 wt. % and in particular 20 to 55 wt. %, relative to the sol.

The $SiO_2$ particles of the sol (a) are present in a liquid, organic dispersion agent. The liquid, organic dispersion agent preferably contains at least one diol, at least one hydroxy (meth)acrylate, at least one di(meth)acrylate or mixtures of these compounds. Those liquid, organic dispersion agents which contain hexanediol diacrylate, 2-hydroxyethyl methacrylate, triethylene glycol dimethacrylate, bisphenol-A-glycidyl methacrylate, a urethane dimethacrylate or mixtures of these compounds are particularly preferred. Particularly advantageous mixtures of liquid, organic dispersion agent are mixtures of triethylene glycol dimethacrylate (TEGDMA), bisphenol-A-glycidyl methacrylate and the urethane dimethacrylate of 2-hydroxyethyl methacrylate (HEMA) and 2,2,4-trimethylhexamethylene diisocyanate (TMDI). It is preferred that the dispersion agent contains at least one polymerizable compound.

The $SiO_2$ particles of the silica organosol (a) are organically modified at the surface. Particularly advantageous is a modification with functional or polymerizable groups, in particular acrylate or methacrylate groups capable of polymerization which, after the polymerization of a sol (a) which contains dispersion agents capable of polymerization, produce a covalent bond of the dispersed $SiO_2$ particles with the polymeric matrix.

The $SiO_2$ sol (a) used in the dental material according to the invention is obtainable by known methods and also commercially. Thus, such a sol can be obtained from commercial colloidal solutions of amorphous silica in water by first modifying the surface of the $SiO_2$ particles by reaction, e.g. with 3-(meth)acryloyloxypropyl trialkoxy silane, then exchanging the water for a volatile alcohol, e.g. isopropanol, and finally replacing the alcohol with the desired dispersion agent, e.g. 2-hydroxyethyl methacrylate or triethylene glycol dimethacrylate. Particularly suitable commercially available $SiO_2$ sols are supplied under the name Highlink®-OG by Société Francaise Hoechst. In these non-opaque $SiO_2$ sols, the $SiO_2$ particles are surface-modified so as to be compatible with various solvents and dispersion agents, such as diols, hydroxy(meth)acrylates or di(meth)acrylates. Types usable according to the invention are in particular Highlink®-OG 103-53, Highlink®-OG 100, Highlink®-OG 2-IV, Highlink®-OG 3-IV and Highlink®-OG 4-IV.

It has surprisingly been shown that, even when using $SiO_2$ sol (a) with a very high $SiO_2$ content, the dental material according to the invention displays a lower viscosity than dental materials which are filled with a corresponding quantity of conventional silica acid in which the $SiO_2$ particles are however present in agglomerated form.

The dental material according to the invention can in addition to the silica organosol (a) also contain at least one polymerizable organic binder (b). This is usually employed in a quantity of 0 to 80 wt. % and in particular 0 to 50 wt. % in the dental material.

Suitable as polymerizable organic binder are all binders which can be used for a dental material, in particular monofunctional or polyfunctional (meth)acrylates, which can be used alone or in mixtures. Preferred examples of these compounds are methyl (meth)acrylate, isobutyl (meth)acrylate, cyclohexyl (meth)acrylate, tetraethylene glycol di(meth)acrylate, diethylene glycol di(meth)acrylate, ethylene glycol di(meth)acrylate, polyethylene glycol di(meth)acrylate, butanediol di(meth)acrylate, hexanediol di(meth)acrylate, decanediol di(meth)acrylate, dodecanediol di(meth)acrylate, bisphenol-A-di(meth)acrylate, 2,2-bis-4-(3-methacryloxy-2-hydroxy-propoxy)-phenylpropane (bis-GMA) and the products of the reaction of isocyanates, in particular di- and/or triisocyanates, with OH group-containing (meth)acrylates. Particularly preferred examples of the last-mentioned products are obtainable by reaction of 1 mol of hexamethylene diisocyanate with 2 mol of 2-hydroxyethyl methacrylate and of 1 mol of tri-(6-isocyanatohexyl)biuret with 3 mol of 2-hydroxyethyl (meth)acrylate.

Particularly preferred polymerizable organic binders (b) are triethylene glycol dimethacrylate, bisphenol-A-glycidyl methacrylate, urethane dimethacrylate of 2,2,4-trimethylhexamethylene diisocyanate (TMDI) and 2-hydroxyethyl methacrylate (HEMA), trimethylolpropane trimethacrylate or pentaerythritol tetramethacrylate.

In addition to the $SiO_2$ sol (a), the dental material according to the invention can also contain conventional inorganic or organic particle-shaped fillers (c). These fillers (c) are typically used in a quantity of 0 to 90 wt. %, in particular 0 to 75 wt. %, in the dental material.

Examples of preferred fillers (c) are precipitated or pyrogenic silicas, calcium carbonate, calcium hydroxide, glass fillers or X-ray-opaque substances such as ytterbium fluoride, barium sulphate and barium hydroxide.

In order to achieve a better adhesion and binding-in of these conventional fillers, they are silanized with silanes, such as methacryloyloxyalkyl silanes, e.g. the commercial 3-methacryloyloxypropyl trimethoxysilane.

The dental material according to the invention can also contain (d) at least one polymerization initiator and optionally an accelerator.

The dental material according to the invention can be hot-, cold- or light-polymerized. The known peroxides such as dibenzoyl peroxide, dilauroyl peroxide, tert.-butylperoctoate or tert.-butylperbenzoate can be used as initiators for hot polymerization. Moreover, 2,2'-azoisobutyric acid nitrile (AIBN), benzpinacol and 2,2'-dialkylbenzpinacols are also suitable.

For example, benzophenone and derivatives thereof as well as benzoin and derivatives thereof can be used as initiators for photopolymerization. Other preferred photoinitiators are the α-diketones, such as 9,10-phenanthrenequinone, diacetyl, furil, anisil, 4,4'-dichlorobenzyl and 4,4'-dialkoxybenzyl. Camphor quinone is particularly preferably used. Moreover, the group of the acyl phosphine oxides is also highly suitable for the initiation of photopolymerization. In order to accelerate the initiation, the photoinitiators are used preferably together with a reducing agent, particularly preferably with an amine, in particular an aromatic amine.

Radical-supplying redox systems, for example benzoyl or lauroyl peroxide together with amines, such as N,N-dimethyl-p-toluidine, N,N-dihydroxyethyl-p-toluidine or other structurally related amines, are used as initiators for cold polymerization.

The combination of photoinitiators with different redox systems has proved effective especially in the case of dental materials for the cementing of dental restorations, such as for example glass ceramic inlays, onlays, partial crowns and crowns. Combinations of camphor quinone, benzoyl peroxide and amines such as, for example, N,N-dimethyl-p-toluidine and/or N,N-cyanoethyl-methylaniline are preferred.

The concentration of initiators and accelerators (d) preferably lies in the range from 0.05 to 1.5 wt. %, particularly preferably in the range from 0.2 to 0.8 wt. %, relative to the quantity of monomers used in the dental material.

It is also possible that the dental material according to the invention is present at least partially in polymerized form.

The dental material according to the invention is used particularly advantageously as a filling composite, fixing cement or adhesive. The reduced polymerization shrinkage and the improved mechanical properties of these materials prove to be a particular advantage here.

When the dental material is used as a dental adhesive, the sol of non-agglomerated $SiO_2$ particles (a) is combined in particular with multifunctional polymerizable organic dispersion agents, often also referred to as crosslinking monomers, and/or binders, such as triethylene glycol dimethacrylate, bisphenol-A-glycidyl methacrylate, urethane methacrylate of HEMA and TMDI. The obtained dental adhesives according to the invention show a clearly lower viscosity compared with systems which are filled with highly-dispersed silicic acid, and a reduced abrasivity of the polymer matrix and a reduction in polymerization shrinkage are to be recorded as further advantages.

When the dental material according to the invention is used as a filling composite, conventional inorganic or organic particle-shaped fillers (c) are customarily also used in addition to the sol (a) and the organic binder (b). Fixing cements are obtained in the case of a low degree of filling and filling materials in the case of a high degree of filling. Moreover, a reinforcement with fibers, e.g. short- or long-glass fibers as well as cellulose or polyamide fibers, is also possible.

Finally, the dental material according to the invention can also contain conventional auxiliaries and additives, such as dyes, pigments, thixotropic agents, stabilizers e.g. hydroquinone monomethylether (MEHQ) or 2,6-di-tert.-4-methylphenol (BHT), flavouring agents or microbicidal substances.

The subject-matter of the invention is also the use of the filled and polymerizable material defined above as a dental material. As mentioned above, this material is characterized by containing (a) a sol of amorphous $SiO_2$ particles in a liquid, organic dispersion agent, the $SiO_2$ particles being organically surface modified, having an average size of 10 to 100 nm and being non-agglomerated.

The material is employed in a manner conventional for dental materials. This manner is essentially characterized by applying the material to a natural or artificial tooth or a part thereof or to another dental material, and curing it by polymerization.

The invention is explained in more detail below with reference to examples.

EXAMPLES

The following substances were used in the examples:
Monomers:
  hexanediol diacrylate (HDDA),
  triethylene glycol dimethacrylate (TEGDMA),
  bisphenol-A-glycidyl methacrylate (bis-GMA),
  urethane dimethacrylate of HEMA and TMDI, referred to as UDMA
Silica organosols (a):
  Highlink®-OG 103-53 (Société Francaise Hoechst): 50 wt. % $SiO_2$, 50 nm particle size, HDDA as dispersion agent, viscosity: 270 mPa.s/20° C.,
  Highlink®-OG 2-IV (Société Francaise Hoechst): 51.7 wt. % $SiO_2$, 50 nm particle size, TEGDMA as dispersion agent, viscosity: 750 mPa.s/20° C.,
  Highlink®-OG 4-IV (Société Francaise Hoechst): 48.7 wt. % $SiO_2$, 50 nm particle size, a mixture of TEGDMA (47.0 wt. %), bis-GMA (28.0 wt. %) and UDMA (25.0 wt. %) as dispersion agent, viscosity: 3.0 mPa.s/20° C.,
Conventional fillers:
  Silanized barium aluminium silicate glass powder (Schott), grain size <7 µm, referred to as BaG,
  Ytterbium fluoride (Rhône-Poulenc) ($YbF_3$),
  Sphärosil, $SiO_2$—$ZrO_2$ mixed oxide (Tokoyama Soda), secondary grain size <7 µm;
Photoinitiator+accelerator:
  Mixture of camphor quinone (CC) and N-(2-cyanoethyl)-N-methylaniline (CEMA).

Example 1

Dental Adhesive With Silica Organosol Containing HDDA as Dispersion Agent

A transparent mixture, usable as dental adhesive, of 99.2 wt. % Highlink® OG 103-53 with 0.3 wt. % CC and 0.5 wt. % CEMA and, as comparison, a mixture of 99.2 wt. % HDDA with 0.3 wt. % CC and 0.5 wt. % CEMA were polymerized by illumination for 6 minutes with a dental radiation source (Spectramat, Fa. Vivadent). The polymerization shrinkage (AV) was calculated from the difference between the monomer and polymer density determined by gas pyknometry, and the bending strength (BF) and bending E modulus (BEM) were determined in accordance with ISO standard 4049 (1988). The ball pressure hardness (KDH) of the polymerizates was measured according to DIN 53456 (1973).

| Material with | ΔV (vol-%) | BF (MPa) | BEM (GPa) | KDH (MPa) |
| --- | --- | --- | --- | --- |
| Highlink® OG 103-53 (invention) | 7.5 | 44 | 2.73 | 149 |
| HDDA (comparison) | 13.1 | 39 | 1.73 | 74 |

Example 2

Dental Adhesive or Varnish with Silica Organosols with Different Dispersion Agents Analogously to Example 1, transparent mixtures of (1.) 99.2 wt. % Highlink® OG 2-IV or (2.) Highlink® OG 4-IV were polymerized with in each case 0.3 wt. % CC and 0.5 wt. % CEMA and, as comparative examples, mixtures of (3.) 99.2 wt. % TEGDMA or (4.) a combination of TEGDMA (46.6 wt. %), bis-GMA (27.8 wt. %) and UDMA (24.8 wt. %) were polymerized with in each case 0.3 wt. % CC and 0.5 wt. % CEMA. The obtained polymers had the following properties.

| No. | Material with | ΔV (vol-%) | BF (MPa) | BEM (GPa) |
| --- | --- | --- | --- | --- |
| 1. | Highlink® OG 2-IV (invention) | 8.6 | 55 | 2.80 |
| 3. | TEGDMA (comparison) | 12.7 | 47 | 1.22 |
| 2. | Highlink® OG 4-IV (invention) | 6.1 | 88 | 3.41 |
| 4. | TEGDMA/bis-GMA/UDMA (comparison) | 8.0 | 83 | 1.97 |

These results show that, compared with materials having no silica organosol, the materials according to the invention display a reduction in the polymerization shrinkage and an improvement in the mechanical properties and in the material hardness, so that they are particularly suitable as dental adhesives or varnishes.

Mixtures, prepared as comparative examples, of the listed monomer components with conventional fillers show that in the case of pyrogenic silica, e.g. OX-50, only opaque mixtures with a small through-hardening depth are accessible or in that of precipitated silica, e.g. HDK 2000

(Wacker-Chemie GmbH), higher degrees of filling are not achievable due to the extreme thickening effect of this silica.

Example 3

Composites of Silica Organosols with Different Dispersion Agents

Composite pastes M1 to M6 were prepared in a planetary kneader (Linde) having the following composition (all data in wt. %).

|  | M-1 | M-2 * | M-3 | M-4 * | M-5 | M-6 *** |
|---|---|---|---|---|---|---|
| Highlink ® OG 103-53 | 24.0 | — | — | — | — | — |
| HDDA | — | 24.0 | — | — | — | — |
| Highlink ® OG 2-IV | — | — | 26.0 | — | — | — |
| TEGDMA | — | — | — | 26.0 | — | 13.3 |
| Highlink ® OG 4-IV | — | — | — | — | 28.4 | — |
| Bis-GMA | — | — | — | — | — | 7.9 |
| UDMA | — | — | — | — | — | 7.2 |
| BaG | 14.0 | 14.0 | 13.6 | 13.6 | 19.5 | 19.5 |
| Spharosil | 13.5 | 13.5 | 13.1 | 13.1 | 18.9 | 18.9 |
| YbF$_3$ | 48.3 | 48.3 | 47.1 | 47.1 | 33.0 | 33.0 |
| CC + CEMA | 0.2 | 0.2 | 0.2 | 0.2 | 0.2 | 0.2 |

*** Comparative examples

These pastes were then vented for 10 minutes at 200 mbar and polymerized analogously to Example 1. The obtained polymers had the following properties:

| Material | ΔV (vol-%) | BF (MPa) | BEM (GPa) |
|---|---|---|---|
| M-1 | 4.4 | 104 | 12.3 |
| M-2 (comparison) | 5.5 | 100 | 6.3 |
| M-3 | 2.4 | 123 | 13.6 |
| M-4 (comparison) | 6.2 | 117 | 6.4 |
| M-5 | 2.5 | 127 | 13.6 |
| M-6 (comparison) | 4.3 | 108 | 6.7 |

These results show that the use of the silica organosols employed according to the invention as a component of dental composites leads to a reduction in the shrinkage and to an improvement in the mechanical properties.

We claim:

1. A method of applying a dental material selected from the group consisting of filling composites, fixing cements, and adhesives to a tooth comprising:
    applying the dental material, which comprises:
        a sol of amorphous SiO$_2$ particles in a liquid, organic dispersion agent, wherein the SiO$_2$ particles are organically surface treated, have an average size of 10 to 100 nm and are non-agglomerated, and
    curing, the dental material.
2. The method according to claim 1, wherein the tooth is selected from the group consisting of a natural tooth, an artificial tooth, and a part thereof.
3. The method according to claim 1, wherein the dental material is selected from the group consisting of a filling composite, a fixing cement, and a dental adhesive.
4. The method according to claim 1, wherein the dental material comprises 1 to 50 wt. % of the sol.
5. The method according to claim 1, wherein the sol comprises 10 to 70 wt. % SiO$_2$ particles, relative to the sol.
6. The method according to claim 1, wherein the liquid, organic dispersion agent comprises at least one polymerizable compound.
7. The method according to claim 1, wherein the liquid, organic dispersion agent comprises a compound selected from the group consisting of
    at least one diol,
    at least one hydroxy (meth)acrylate,
    at least one di(meth)acrylate, and
    mixtures of the above compounds.
8. The method according to claim 1, wherein the liquid, organic dispersion agent comprises a compound selected from the group consisting of
    hexanediol diacrylate,
    2-hydroxyethyl methacrylate,
    triethylene glycol dimethacrylate,
    bisphenol-A-glycidyl methacrylate,
    a urethane dimethacrylate, and
    mixtures of the above compounds.
9. The method according to claim 1, wherein the dental material further comprises:
    at least one polymerizable organic binder.
10. The method according to claim 9, wherein the polymerizable organic binder is selected from the group consisting of
    triethylene glycol dimethacrylate,
    bisphenol-A-glycidyl methacrylate,
    the urethane dimethacrylate of 2,2,4-trimethylhexamethylene diisocyanate and 2-hydroxyethyl methacrylate,
    trimethylolpropane trimethacrylate, and
    pentaerythritol tetramethacrylate.
11. The method according to claim 1, wherein the dental material further comprises:
    inorganic or organic particle-shaped fillers.
12. The method according to claim 1, wherein the dental material further comprises:
    at least one polymerization initiator.
13. The method according to claim 1, wherein the dental material is at least partially polymerized.
14. The method according to claim 1, wherein the sol comprises 20 to 55 wt. % SiO$_2$ particles.
15. The method according to claim 12, wherein the dental material further comprises:
    an accelerator.

* * * * *